United States Patent
Cinar et al.

(10) Patent No.: US 8,883,931 B2
(45) Date of Patent: Nov. 11, 2014

(54) POLYNITRONES AND USE THEREOF FOR CROSS-LINKING UNSATURATED POLYMERS

(75) Inventors: Hakan Cinar, Neuss (DE); Helmut Ritter, Wuppertal (DE)

(73) Assignee: Heinrich-Heine-Universitat, Dusseldorf (DE)

( * ) Notice: Subject to any disclaimer, the term of this patent is extended or adjusted under 35 U.S.C. 154(b) by 33 days.

(21) Appl. No.: 12/747,582

(22) PCT Filed: Dec. 10, 2008

(86) PCT No.: PCT/EP2008/010487
§ 371 (c)(1), (2), (4) Date: Jun. 11, 2010

(87) PCT Pub. No.: WO2009/074310
PCT Pub. Date: Jun. 18, 2009

(65) Prior Publication Data
US 2010/0273910 A1    Oct. 28, 2010

(30) Foreign Application Priority Data
Dec. 12, 2007 (DE) .......................... 10 2007 059 733

(51) Int. Cl.
| | |
|---|---|
| *C08C 19/22* | (2006.01) |
| *C08L 67/00* | (2006.01) |
| *C08G 18/10* | (2006.01) |
| *C09D 5/03* | (2006.01) |
| *C08K 5/00* | (2006.01) |
| *C09D 5/34* | (2006.01) |
| *C08K 5/32* | (2006.01) |
| *C09D 7/00* | (2006.01) |
| *C07C 291/02* | (2006.01) |

(52) U.S. Cl.
CPC . *C08K 5/32* (2013.01); *C09D 5/033* (2013.01); *C08K 5/0025* (2013.01); *C09D 5/34* (2013.01); *C09D 7/005* (2013.01); *C07C 291/02* (2013.01)
USPC ............................. 525/377; 523/500; 528/63

(58) Field of Classification Search
USPC ............................. 525/377; 523/500; 528/63
See application file for complete search history.

(56) References Cited

U.S. PATENT DOCUMENTS

| | | | | | |
|---|---|---|---|---|---|
| 3,390,133 | A | * | 6/1968 | Breslow | 525/332.5 |
| 3,812,206 | A | * | 5/1974 | Banks et al. | 525/539 |
| 3,988,229 | A | * | 10/1976 | Pacifici et al. | 522/78 |
| 5,219,710 | A | * | 6/1993 | Horn et al. | 430/270.1 |
| 5,273,863 | A | | 12/1993 | Horn et al. | |
| 6,162,579 | A | * | 12/2000 | Stengel et al. | 430/272.1 |
| 7,989,488 | B2 | * | 8/2011 | Erben et al. | 514/444 |
| 2010/0016349 | A1 | * | 1/2010 | Becker et al. | 514/299 |

FOREIGN PATENT DOCUMENTS

| | | | |
|---|---|---|---|
| DE | 1 694 370 A1 | | 2/1971 |
| JP | 2007-070439 A | * | 3/2007 |
| JP | 2007070439 A | | 3/2007 |

OTHER PUBLICATIONS

Vretik, L., et al. "1,3-Dipolar Cycloaddition in Polymer Synthesis. 1. Polyadducts with Flexible Spacers Derived from Bis(N-methylnitrone)s and Bis(N-phenylmaleimide)s". Macromolecules (online). 2003, vol. 36, No. 17, pp. 6340-6345. XP-002516797.
An English translation of an Official Action issued in Japanese Patent Application No. 2010-537308; mailed on Jul. 24, 2012.

* cited by examiner

*Primary Examiner* — Tae H Yoon
(74) *Attorney, Agent, or Firm* — Nath, Goldberg & Meyer; Joshua B. Goldberg; Tanya E. Harkins

(57) ABSTRACT

The present invention relates to polyfunctional nitrones (optionally in the form of nitrone-terminated polymers) and to their use as crosslinking agents and matting agents, preferably for producing stable molding compounds, knifing fillers, and use thereof in inks, coatings, and adhesives. Low crosslinking temperatures characterize the invention. Through the use of polyfunctional nitrones it is possible for all unsaturated polymers to be cured, solidified and/or structured at low temperatures, preferably without use of a catalyst. Depending on the amount of nitrone-terminated polymers and/or low molecular mass polyfunctional nitrone used it is possible to exert a strong influence over the optical and the mechanical properties of the coated surfaces. By optical properties are meant, among others, the gloss of the coating systems and the surface structuring, e.g., the matte effect.

9 Claims, 6 Drawing Sheets

UP powder coating (P-UP, 12)
without polynitrone

UP powder coating (P-UP, 12)
with 1 wt.% polynitrone (DN-10, 2)

Light-micrographs of coated polyester films after UV curing

POLYNITRONES AND USE THEREOF FOR CROSS-LINKING UNSATURATED POLYMERS

This is a National Phase Application filed under 35 U.S.C. §371 as a national stage of PCT/EP2008/010487, filed on Dec. 10, 2008, claiming the benefit of German Patent Application 10 2007 059 733.0, filed on Dec. 12, 2007, the content of each of which is hereby incorporated by reference in its entirety.

The invention relates to polynitrones and to the use thereof for crosslinking unsaturated polymers, and also to a curable composition comprising (a) a polynitrone, (b) an unsaturated polymer, (c) optionally filers, and (d) optionally pigments, and to use thereof as adhesive, knifing filler, sprayable high-build filler, powder coating and/or coating based on solvent systems. The invention further relates to crosslinking products obtainable by curing the curable composition of the invention. The invention relates finally to polynitrone-terminated polyurethanes and unsaturated polyesterurethane polynitrones and also to processes for preparing them.

"Nitrones" are known within the field of organic chemistry. The term typically refers to compounds containing the structural element

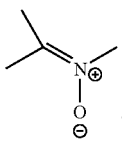

Nitrones are also referred to as azomethine oxides.

Within this field of art, various reactions of nitrones have been demonstrated. Known, for example, was the stereospecific addition to dimethyl maleate or dimethyl fumarate (Huisgen et al., Chem. Ber. 102, 736-745, 1969). Concerning the interaction of nitrone groups and polymers, little is known in this field of art. For example, the installation of nitrones onto the side chains of polyacrylates for application as waveguides was described in U.S. Pat. No. 5,273,863. The UV sensitivity of the nitrone groups strongly modified the refractive index of the material under UV irradiation. Also known, from U.S. Pat. No. 3,991,261, is the use of monofunctional, nitrone-containing compounds for enhancing the shelf life of adhesives and sealants based on (meth)acrylic ester and organic hydroperoxide initiators. The functionalization of rubber polymers on the basis of polydienes represents another example of the use of nitrones and is disclosed in EP 1 739 098. In that case, various lithium-terminated rubber polymers, such as polybutadiene, polyisoprene, poly(styrene-butadiene) or poly(styrene-isoprene-butadiene), for example, react with monofunctional nitrones to give a hydroxylamine, so producing better interactions between the rubber polymers and fillers, such as carbon black or silica gels, for example. The properties of the materials developed therefrom, such as tires, for example, are improved.

Polymers with unsaturated groups can be used generally for powder coating systems. Powder coatings possess environmental advantages over conventional coating systems. They are applied without solvent and hence without emissions. "Overspray", in other words coating-material particles which do not land on the substrate to be coated, is retained and used again. Hence it is possible to utilize virtually 100 percent of the powder coating material.

Important fields of application for powder coatings are household appliances such as so-called white goods, by which are meant, for example, refrigerators, washing machines, dishwashers, freezers, etc. In addition, computer housings, satellite antennas, lamp housings, and metal furniture are often powder coated. Further important areas of application are facade elements, especially those made of aluminum, garage doors, components for installation in or on automobiles, and machine housings.

The customary prior-art powder coating production process is illustrated in FIG. 1. The key to FIG. 1 is as follows: 1=weighing, 2=mixing, 3=extruding, 4=cooling, 5=preliminary fractionating, 6=grinding, and 7=screening. The solid base materials for the coating, such as binders, curing agents, pigments, fillers, and additives, are mixed and, in an extruder at 100-140° C., are kneaded and dispersed in a highly viscous state to form a homogeneous material.

Prior to actual powder application, the powder coatings manufactured according to FIG. 1 are typically fluidized by supply of air and conveyed in this fluidic state to the gun. There, the powder is charged by charging at an electrode by means of high voltage. The thus-conditioned powder is deposited on a suspended article.

The application of the powder coating technology has to date been limited by the fact that the coating operation with powder coatings proceeds with high baking temperatures. For instance, weathering-stable, thermosetting powder coatings crosslink generally at temperatures above 160° C. At these temperatures it has to date not been possible to coat non-heat-resistant substrates such as wood and crosslinking products, or even metallic alloys having specific properties.

The UV powder coating technology is a technique where the powder coatings are cured at low temperatures by UV radiation. Through this technology it is possible to powder coat the surfaces of thermally sensitive products, such as wood surfaces, medium-density fiberboard (MDF), plastics surfaces, or paper, for example. Following the deposition of the powder on the substrate, the applied panels are heated in an oven (100-140° C.) and then cured by UV. The curing reaction in the case of the UV technology is usually a free-radical polymerization of acrylic ester derivatives. This reaction is started by a photoinitiator, which is excited by the UV light and forms free radicals.

The photochemical formation of the free radicals hence initiates a further polymerization, and so, within a few seconds, three-dimensional networks are produced. Raw materials used as binders are typically polyfunctional acrylic ester derivatives, epoxy resins, polyethers, and polyurethanes, or else a combination of an unsaturated polyester and a polyfunctional vinyl ether crosslinker.

The UV-curable powder coatings feature low stressing of the article to be coated, relatively short cure times, and good optical properties. Countering these features, however, are unresolved difficulties. These include in particular the minimizing of coat thicknesses and the difficulty of surface structuring. Depending on where the powder coatings are employed, there are many sectors, such as the furniture industry, for example, where it is necessary to reduce the gloss of the powder coating. Owing to the limited coat thicknesses affecting the radiation-curable powder coatings, numerous techniques with which the conventionally, thermally curable powder coatings are normally structured and modified, as for example by means of pigments, fillers or solid additives, cannot be used. Furthermore, the matting of UV-curable powder coatings is difficult. One complicated option is the mixing of amorphous and crystalline resins. Another complicated method for the matting of radiation-curable coatings is described by U.S. Pat. No. 6,777,027 B2, where the combination of a free-radically curable and a cationically curable binder resin produces matting in the powder coating described. The methods used, however, are expensive and involve complicated procedures.

The object of the invention, then, was to find a curable material which does not have the stated disadvantages of the existing systems. The material is to cure rapidly at moderate temperatures, is to accept a variety of pigments and fillers, and, across wide areas, is to satisfy the physical and chemical requirements of industry. The curable material is to make it possible for the degree of matting to be influenced.

An object of the invention was likewise to provide an advantageous method of curing.

A particular object of the invention was to provide a curable composition present in the form of a 1-component system (referred to hereinafter as 1K system), or of a 2-component system (referred to hereinafter as 2K system).

It has been possible to achieve these objects through the use of what are called polynitrones, more particularly through the use of polynitrones together with unsaturated polymers.

The invention accordingly provides the use of polynitrones for crosslinking unsaturated polymers.

The invention further provides a curable composition comprising
(a) a polynitrone,
(b) an unsaturated polymer,
(c) optionally fillers, and
(d) optionally pigments.

The invention additionally provides a process for preparing a crosslinking product, comprising the steps of
(i) providing the curable composition of the invention, and
(ii) curing the composition.

Likewise provided by the invention are crosslinking products obtainable by this process, and their use for producing glass fiber reinforced polyester components, preferably in shipbuilding.

The invention likewise provides specific polynitrones as such, more particular polynitrone-terminated polyurethanes, and also a process for preparing them.

The invention provides, finally, an unsaturated polyesterurethane polynitrone and also a process for its preparation.

Figure 1:
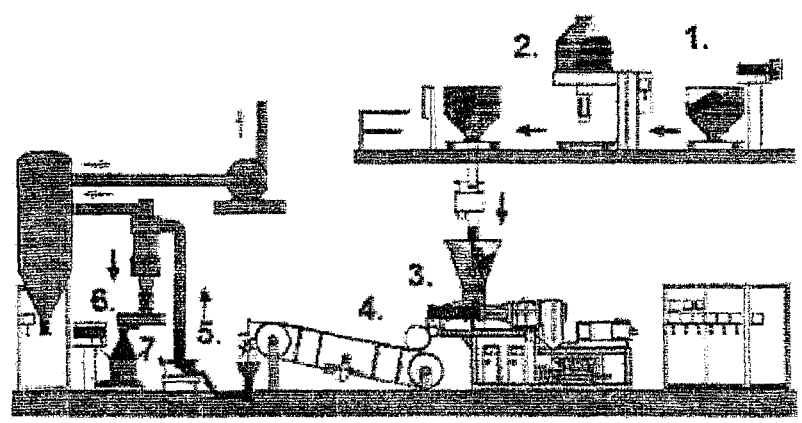
FIG. 1 depicts customary powder coating production process, as follows: 1=weighing, 2=mixing, 3=extruding, 4=cooling, 5=preliminary fractionating, 6=grinding and 7=screening.

The inventors of the present patent specification have unexpectedly found that polynitrones can be used advantageously for crosslinking unsaturated polymers. Crosslinking here means the formation of covalent or ionic bonds between polymer chains. As result of the crosslinking, typically, a so-called "three-dimensional structure" is formed.

In particular it has been found that polynitrones can be used for the advantageous modification of the mechanical and/or optical properties of an unsaturated polymer. For example, the mechanical properties may be modified advantageously by hardening of the unsaturated polymer. It is likewise possible, alternatively or additionally, for the optical properties to be advantageously modified by matting.

In the context of this invention the term "polynitrone" refers to a polyfunctional nitrone, i.e., the term "polynitrone" describes an organic compound which has two or more nitrone groups. The polynitrones used preferably have 2 to 12, more preferably 2 to 5, more particularly 3 to 4 nitrone groups.

In one preferred embodiment the polynitrone used in accordance with the invention is a compound in accordance with the general formula I,

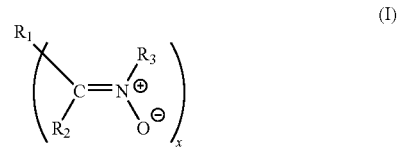

in which x is a natural number from 2 to 12, more preferably 2, 3 or 4. The radicals $R_1$, $R_2$ or $R_3$ may generally be any desired organic radicals. Preferably $R_1$ is an optionally substituted linear, cyclic or branched alkylene group, alkyleneoxy group, arylene group, aryleneoxy group, naphthalene group or combinations thereof. Preferably, furthermore, $R_2$ and $R_3$ independently of one another are hydrogen or an optionally substituted linear or branched alkyl group, aryl group, heteroaryl group, alkylaryl group, alkoxy group, cycloalkyl group or combination thereof.

More preferably the radical $R_1$ comprises one or more of the following groups:

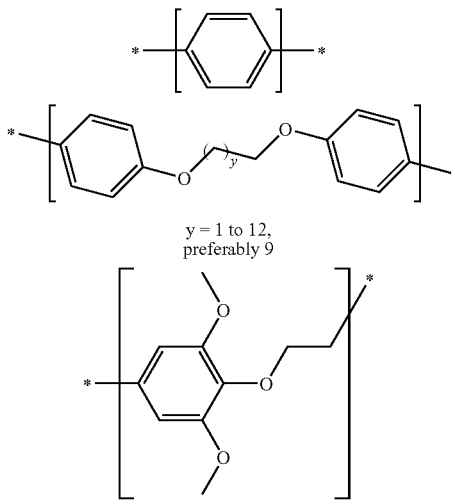

$R_2$ and $R_3$ are more preferably a hydrogen atom or a $C_1$-$C_6$ alkyl group. More particularly $R_2$ is a hydrogen atom. More particularly $R_3$ is a methyl group. In the three structural formulae shown above, the aromatic rings may optionally be substituted in one or more positions.

In another embodiment the radical $R_1$ may be bonded to a polymer. The polymer is preferably selected from polyurethanes, polyesters, unsaturated polyesters, poly(meth)acrylates, polysaccharides or combinations thereof. As described later on in more detail, $R_1$ in the case of the 1K system is bonded more particularly to an unsaturated polyesterurethane.

The abovementioned polynitrones are used for crosslinking unsaturated polymers. The term "unsaturated polymer" refers typically to a polymer having one or more unsaturated carbon-carbon bonds in the polymer chain.

The degree of unsaturated carbon-carbon bonds can be determined by DIN 53241 and expressed through the unit "meq/g". Typically the unsaturated polymers feature 0.1 to 50, preferably 1 to 20 meq/g.

The unsaturated polymers are preferably selected from polyolefins, polystyrene, polyvinyl alcohol, polyvinyl acetate, polyalkylene glycol, polyethylene oxide, polypropylene oxide, polyacetals, polyurethanes, polyureas, polyamides, polycarbonates, polyketones, polysulfones, phenol-formaldehyde resins, polyesters, polyester acrylates, polyurethane acrylates, cellulose, gelatin, starch, and mixtures thereof.

Particular preference is given to using unsaturated polyesters, unsaturated polyesterurethanes and/or polyesterurethane acrylates or polyesterurethane meth-acrylates, of the kind described in U.S. Pat. No. 6,284,321 B1, for example.

Details will now be given of the unsaturated polyesters that are preferably used.

Unsaturated polyesters generally contemplated are polycondensation products of α,β-ethylenically unsaturated dicarboxylic acids, such as maleic acid, fumaric acid, itaconic acid, mesaconic acid, and citraconic acid, with polyalcohols, such as ethylene glycol, diethylene glycol, propanediols, butanediols, and hexanediols, trimethylolpropane, and pentaerythritol, which may optionally further contain radicals of saturated carboxylic acids, e.g., succinic acid, glutaric acid, adipic acid, phthalic acid, tetrachlorophthalic acid, and also of monofunctional alcohols, such as butanol, tetrahydrofuryl alcohol, and ethylene glycol monobutyl ether, and also of monobasic acids, such as benzoic acid, oleic acid, linseed oil fatty acid, and ricinene fatty acid.

Examples of suitable monomeric unsaturated compounds which can be copolymerized with the unsaturated polyesters include vinyl compounds, such as styrene, vinyltoluene, and divinylbenzene, and also vinyl esters, such as vinyl acetate, and unsaturated carboxylic acids and their derivatives, such as methacrylic acid, methacrylic esters and methacrylonitrile, and also allyl esters, such as allyl acetate, allyl acrylate, diallyl phthalate, triallyl phosphate, and triallyl cyanurate.

Use is made more particularly of unsaturated polyesters which contain maleate groups and fumarate groups.

The unsaturated polymers typically have a weight-average molecular weight of 200 to 500 000 g/mol, preferably of 1000 to 200 000 g/mol, more preferably of 10 000 to 100 000 g/mol.

The polynitrones described above may be used in accordance with the invention in the context of a curable composition.

The invention accordingly provides a curable composition comprising
(a) a polynitrone,
(b) an unsaturated polymer,
(c) optionally fillers, and
(d) optionally pigments.

In principle there are two different embodiments possible for the curable composition of the invention.

In a first embodiment the curable composition of the invention is a 2-component system. This means that the constituents (a) and (b) are present in the form of two compounds. Accordingly, components (a) and (b) are separate compounds which are not joined covalently prior to the onset of curing.

In principle, for this first embodiment of the curable composition of the invention, the explanations given for the abovementioned preferred polynitrones are employed. It is preferred, however, for polynitrones in accordance with the general formula I to be used where the radical $R_1$ is not bonded to a polymer, especially not to an unsaturated polymer.

Likewise used for this first embodiment are the explanations relating to the abovementioned preferred unsaturated polymers.

In this first embodiment of the curable composition of the invention, the polynitrone (a) is present in an amount of 0.1% to 50% by weight, more preferably of 1% to 20% by weight, more particularly 5% to 15% by weight, based on the total weight of the composition.

In a second embodiment of the curable composition of the invention, the curable composition is a 1-component system. This means that the constituents (a) and (b) are present in the form of a polynitrone-terminated unsaturated polymer. Accordingly, components (a) and (b) are united within one compound.

In principle, for this second embodiment of the curable composition of the invention, the explanations given for the abovementioned preferred polynitrones are employed. It is necessary, however, to use polynitrones in accordance with the general formula I where the radical $R_1$ is bonded to an unsaturated polymer.

In the second embodiment of the curable composition of the invention, the united constituents (a) and (b) are preferably an unsaturated polyester polynitrone, more preferably an unsaturated polyesterurethane polynitrone.

For both embodiments the ratio of nitrone groups (from constituent a) to unsaturated carbon-carbon bonds (from constituent b) in the curable composition can be 10:1 to 1:10, preferably 5:1 to 1:5, more particularly 2:1 to 1:2.

Besides the constituents (a) and (b), the curable composition of the invention may optionally comprise the constituents (c) fillers and (d) pigments. Furthermore, the composition may further comprise one or more (e) adjuvants such as, for example, plasticizers and stabilizers. Finally, the curable composition may further comprise (f) photoinitiators. The constituents (a) and (b) are present in the composition of the invention typically in an amount of 30-100% by weight, preferably of 40-99% by weight, more preferably of 55-95% by weight, based on the total weight of the composition.

Fillers (c) contemplated are in principle all organic and inorganic fillers, of the kind described in, for example, Römpp Lexikon Lacke and Druckfarben, Georg Thieme Verlag, Stuttgart, New York, 1998, "fillers", pages 250 to 252.

Examples of suitable fillers are wood flour, saturated organic or organometallic polymers, inorganic minerals, salts or ceramic materials, or organically modified ceramic materials, or mixtures of these substances. Inorganic minerals are used with preference. These may be natural and synthetic minerals. Examples of suitable minerals are silicon dioxide, aluminum silicates, calcium silicates, magnesium silicates, calcium aluminum silicates, magnesium aluminum silicates, calcium magnesium silicates, beryllium aluminum silicates, aluminum phosphate or calcium phosphate, or mixtures thereof.

In the composition of the invention, fillers (c) are present generally in an amount of 0% to 50% by weight, preferably of 5% to 40% by weight, more preferably of 10% to 30% by weight, based on the total weight of the composition.

The composition of the invention may further optionally comprise, as constituent (d), at least one colorant, preferably a pigment. The colorant may be a pigment or a dye. Examples of pigments which can be used are color pigments or effect pigments.

Effect pigments used may be metal flake pigments such as commercial aluminum bronzes, chromatized aluminum bronzes, commercial stainless steel bronzes, and nonmetallic effect pigments, such as pearlescent pigments or interference pigments, for example. For further details, refer to Römpp Lexikon Lacke und Druckfarben, Georg Thieme Verlag, 1998, page 176, effect pigments, and pages 380 and 381, metal oxide-mica pigments to metallic pigments.

Examples of suitable inorganic coloring pigments are titanium dioxide, iron oxides, and carbon black, more particularly carbon black. Examples of suitable organic coloring pigments are thioindigo pigments, indanthrene blue, Cromophthal red, Irgazine orange, and Heliogen green, copper phthalocyan. For further details, refer to Römpp Lexikon Lacke und Druckfarben, Georg Thieme Verlag, 1998, pages 180 and 181, iron-blue pigments to black iron oxide, pages 451 to 453, pigments to pigment volume concentration, page 563 thioindigo pigments, and page 567 titanium dioxide pigments.

In the composition of the invention, colorants, preferably pigments (d), are present generally in an amount of 0% to 30% by weight, preferably of 1% to 20% by weight, more preferably of 2% to 10% by weight, based on the total weight of the composition.

The composition of the invention may further comprise at least one adjuvant (e). Examples of suitable adjuvants are additional oligomers and polymeric binders, UV absorbers, light stabilizers, free-radical scavengers, thermolabile free-radical initiators, deaerating agents, slip additives, polymerization inhibitors, defoamers, emulsifiers, wetting agents, dispersants, adhesion promoters, flow control agents, film-forming assistants, flame retardants, corrosion inhibitors, free-flow aids, waxes, and matting agents.

In the composition of the invention, adjuvants (e) are present generally in an amount of 0% to 20% by weight, preferably of 0.1% to 10% by weight, more preferably of 1% to 5% by weight, based on the total weight of the composition.

In one embodiment it is preferred for the curable composition of the invention to contain no catalysts that catalyze the crosslinking of the unsaturated carbon-carbon bonds in constituent (b). In an alternative embodiment the curable composition of the invention may comprise one or more photoinitiators (f).

One example of a suitable photoinitiator is Irgacure®.

Photoinitiators may be used in an amount of 0-5% by weight, preferably of 0.01-3% by weight, more preferably 0.4% to 2.0% by weight, based on the total weight of the composition.

Photoinitiators (f) are used more particularly when the polynitrones (a) are intended to serve as matting agents.

The curable composition of the invention finds use preferably as adhesive, knifing filler, sprayable high-build filler, powder coating and/or coating based on solvent systems. The invention accordingly also provides an adhesive, a knifing filler, a sprayable high-build filler, a powder coating and/or coating based on solvent systems, comprising the composition of the invention. The composition of the invention is preferably in the form of a powder coating.

The curable composition of the invention can be processed by curing (i.e., by crosslinking) to form a crosslinking product. The curing (i.e., the crosslinking) takes place through appropriate heating of the curable composition.

The invention accordingly also provides a method of producing a crosslinking product, comprising the steps of
(i) providing a curable composition of the invention, and
(ii) curing the composition at temperatures of 20 to 180° C., preferably of 50 to 150° C., more particularly of 60° C. to 120° C.

Likewise provided by the invention is a crosslinking product obtainable by the method of the invention.

The curing/crosslinking can be performed by mixing and heating the constituents of the curable composition. The unsaturated polymer (b) and the polynitrone (a) (or, alternatively, an unsaturated polynitrone-terminated polymer as a 1K system) may be ground to a powder in a customary mill (together if appropriate with constituents (c)-(e)) and mixed. Another possibility for mixing is by means of a solvent system, in which not only the unsaturated polymer but also the polyfunctional nitrones (optionally together with constituents (c)-(e)) are in solution or dispersion. The constituents are first transformed into a uniform mixture and, after the solvent has been removed, curing/crosslinking takes place by heating to the desired temperature.

In the method of the invention the cure time is typically 10 seconds to 2 hours, preferably 20 seconds to 60 minutes, more preferably 30 seconds to 15 minutes, more preferably 1 minute to 10 minutes.

The crosslinking products of the invention are typically dependent on the nature of the unsaturated polymer used. Preferably they are elastically soft to hard crosslinking products. They are preferably inert toward water and organic solvents.

The possible uses of the crosslinking products of the invention are diverse. Examples are dental materials, household appliances, kitchen worktops, general construction industry, bath tubs, and wash basins. The crosslinking products of the invention are used preferably as a coating film. Likewise, the crosslinking products of the invention are used as (preferably glass fiber-reinforced) polyester components, more particularly in shipbuilding.

In addition to the inventive use, the curable composition of the invention, and the crosslinking product of the invention, the preferentially suitable polynitrones per se are also provided by the invention.

The invention therefore also provides polynitrones selected from terephthalaldehyde-bis(N-phenylnitrone), isophthalaldehyde-bis(N-phenylnitrone), isophthal-aldehyde-bis(N-methylnitrone), terephthalaldehyde-bis-(N-butylnitrone), isophthalaldehyde-bis(N-cyclodecyl-nitrone), isophthalaldehyde-bis(N-cyclohexylnitrone), 4,4'-decanediyldioxydi(N-methyl-p-phenylenenitrone), 4,4'-hexanediyldioxydi(N-methyl-p-phenylenenitrone), 4,4'-butanediyldioxydi(N-methyl-p-phenylenenitrone), 4,4'-ethanediyldioxydi(N-methyl-p-phenylenenitrone), and polynitrone-terminated polyurethanes.

By "polynitrone-terminated polyurethane" is meant, generally, a compound which comprises two or more urethane groups and two or more nitrone groups.

In one preferred embodiment this is a polynitrone-terminated polyurethane in accordance with the general formula II

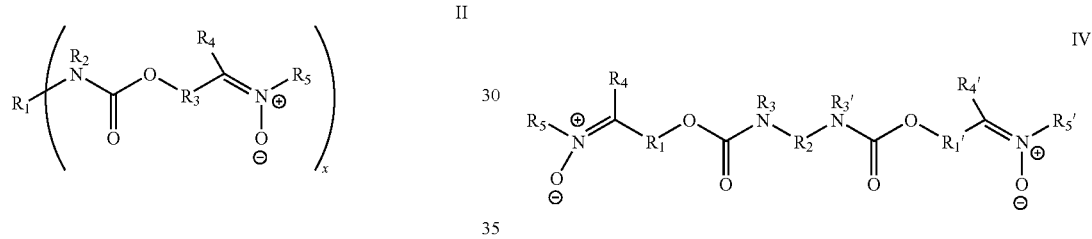

in which x is a natural number from 2 to 12 and $R_1$ to $R_5$ are an organic radical.

Preferably, x is a natural number from 2 to 5, more preferably 3 or 4. $R_1$ and $R_3$ are independently of one another preferably an optionally substituted linear, cyclic or branched alkylene group, alkyleneoxy group, arylene group, aryleneoxy group, naphthalene group or combinations thereof. $R_2$, $R_4$, and $R_5$ are preferably a hydrogen atom or a $C_1$-$C_6$ alkyl group. More particularly, $R_2$ and $R_4$ are a hydrogen atom and $R_5$ is a methyl group.

More particularly provided by the invention is a polynitrone-terminated polyurethane in accordance with the general formula III

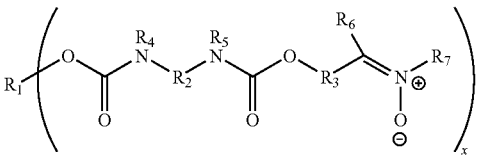

in which x is a natural number from 2 to 20 and $R_1$ to $R_7$ are an organic radical.

Preferably, x is a natural number from 2 to 5, more preferably 3 or 4. $R_1$ and $R_3$ are preferably independently of one another an optionally substituted linear, cyclic or branched alkylene group, alkyleneoxy group, arylene group, aryleneoxy group, naphthalene group or combinations thereof. $R_4$, $R_5$, $R_6$, and $R_7$ are preferably a hydrogen atom or a $C_1$-$C_6$ alkyl group. More particularly, $R_4$, $R_5$, and $R_6$ are a hydrogen atom and $R_7$ is a methyl group. $R_2$ is preferably a diphenylmethane radical, a tolylene radical or an isophorone radical.

More particularly provided, furthermore, by the invention is a polynitrone-terminated polyurethane in accordance with the general formula IV

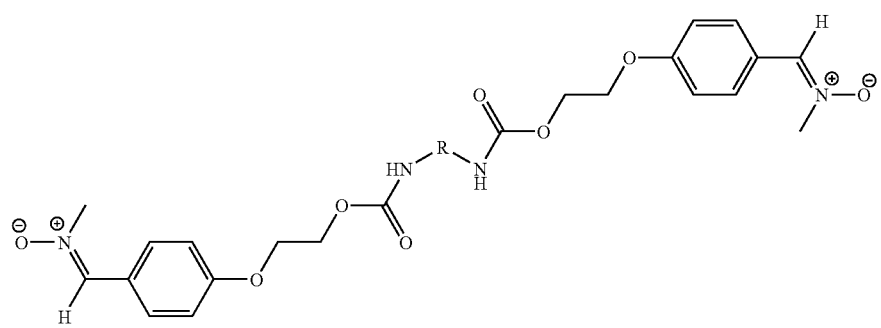

in which $R_1$ to $R_5$ and $R_{1'}$ to $R_{5'}$ are an organic radical.

$R_1$ and $R_{1'}$ are preferably an optionally substituted linear, cyclic or branched alkylene group, alkyleneoxy group, arylene group, aryleneoxy group, naphthalene group or combinations thereof. $R_3$, $R_{3'}$, $R_4$, $R_{4'}$, $R_5$, and $R_{5'}$ are preferably a hydrogen atom or a $C_1$-$C_6$ alkyl group. More particularly, $R_3$, $R_{3'}$, $R_4$, and $R_{4'}$ are a hydrogen atom and $R_5$ and also $R_{5'}$ are a methyl group. $R_2$ is preferably a diphenylmethane radical, a tolylene radical or an isophorone radical.

Examples of compounds of the general formula II, III and/or IV are where R is an organic radical, preferably a diphenylmethane radical, a tolylene radical or an isophorone radical, and anate, IPDI), 1,4- and/or 1,3-bis(isocyanatomethyl) cyclohexane (HXDI), 1,4-cyclohexane diisocyanate, 1-methyl-2,4- and/or -2,6-cyclohexane diisocyanate and/or 4,4'-, 2,4'-, and 2,2'-dicyclohexylmethane diisocyanate; preferred are 2,2'-, 2,4'- and/or 4,4'-diphenylmethane diisocyanate (MDI), 2,4- and/or 2,6-tolylene diisocyanate (TDI), hexamethylene diisocyanate and/or IPDI; in particular, IPDI is used.

A suitable hydroxyaldehyde compound is in principle a compound which has both a hydroxyl function and an aldehyde function. It is preferred to use a 4-hydroxyalkyloxy-3,5-dimethyloxybenzaldehyde in which the alkyl radical comprises 1 to 12 carbon atoms. Examples thereof are methyl, ethyl, propyl or hexyl. Use is made more particularly of 4-hydroxyethyloxy-3,5-dimethoxybenzaldehyde (referred to hereinafter as HEBA). HEBA is therefore likewise provided by the invention.

A suitable hydroxynitrone compound is in principle a compound which has both a hydroxyl function and a nitrone function. Preference is given to using the compound below (which is referred to as HEBN). HEBN is therefore likewise provided by the invention.

(6)

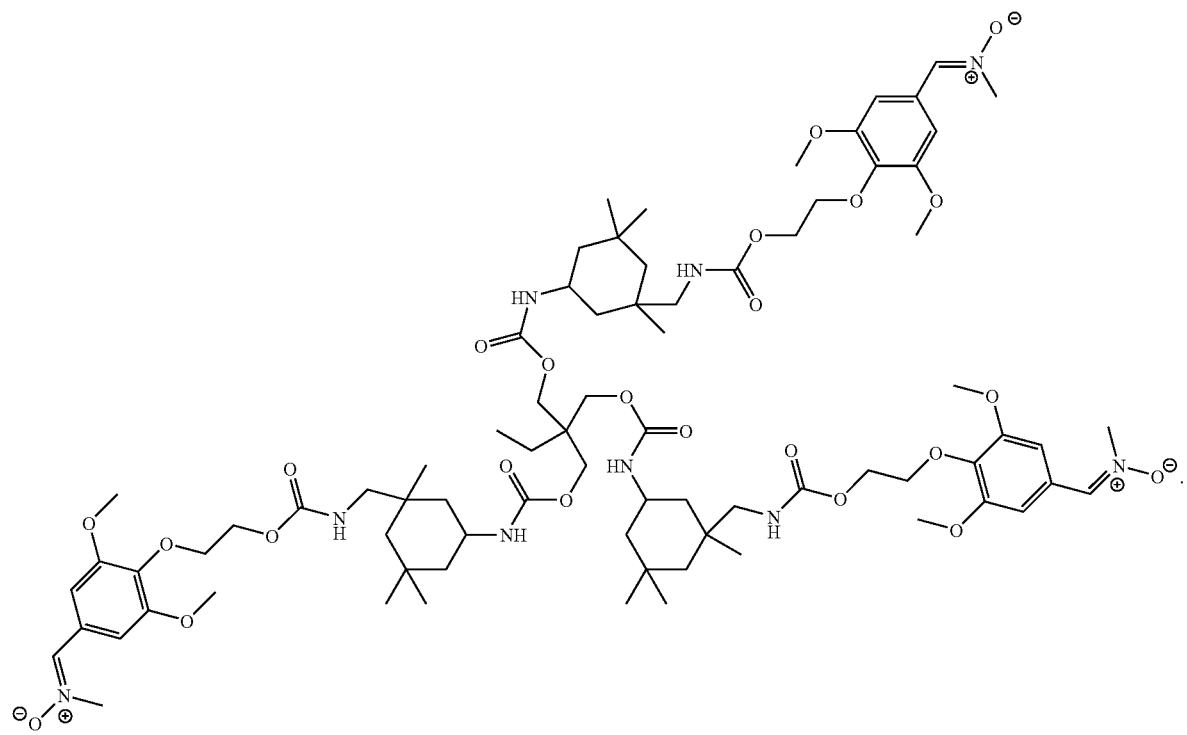

UN-1

The invention further provides a process for preparing a polynitrone-terminated polyurethane of the invention, comprising the steps of
(i) preparing a urethanepolyaldehyde by reacting a polyisocyanate with a hydroxyaldehyde compound (optionally in the presence of a polyfunctional starter molecule), the reaction ratio preferably being selected such that all of the isocyanate groups react, and
(ii) reacting the urethanepolyaldehyde with an N-alkyl-hydroxylamine, preferably with N-methylhydroxylamine, or alternatively
(i) reacting a hydroxyaldehyde compound with an N-alkyl-hydroxylamine, preferably with N-methyl-hydroxylamine, to give a hydroxynitrone compound and
(ii) reacting the reaction hydroxynitro compound resulting from step (i) with a polyisocyanate, the reaction ratio preferably being selected such that all of the isocyanate groups react.

Suitable polyisocyanates are generally the aliphatic, cycloaliphatic, and aromatic isocyanates that are known from the prior art. Examples are 2,2'-, 2,4'- and/or 4,4'-diphenyl-methane diisocyanate (MDI), 1,5-naphthalene diisocyanate (NDI), 2,4- and/or 2,6-tolylene diisocyanate (TDI), diphenyl-methane diisocyanate, 3,3'-dimethyldiphenyl diisocyanate, 1,2-diphenylethane diisocyanate and/or phenylene diisocyanate, tri-, tetra-, penta-, hexa-, hepta- and/or octamethylene diisocyanate, 2-methylpenta-methylene 1,5-isocyanate, 2-ethylbutylene 1,4-diisocyanate, pentamethylene 1,5-diisocyanate, butylene 1,4-diisocyanate, 1-isocyanato-3,3,5-trimethyl-5-iso-cyanatomethylcyclohexane (isophorone diisocy-

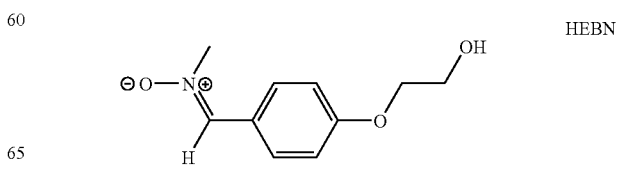

HEBN

The process of the invention for preparing a polynitrone-terminated polyurethane of the invention encompasses two alternatives, which are to be illustrated in the reaction diagram below.

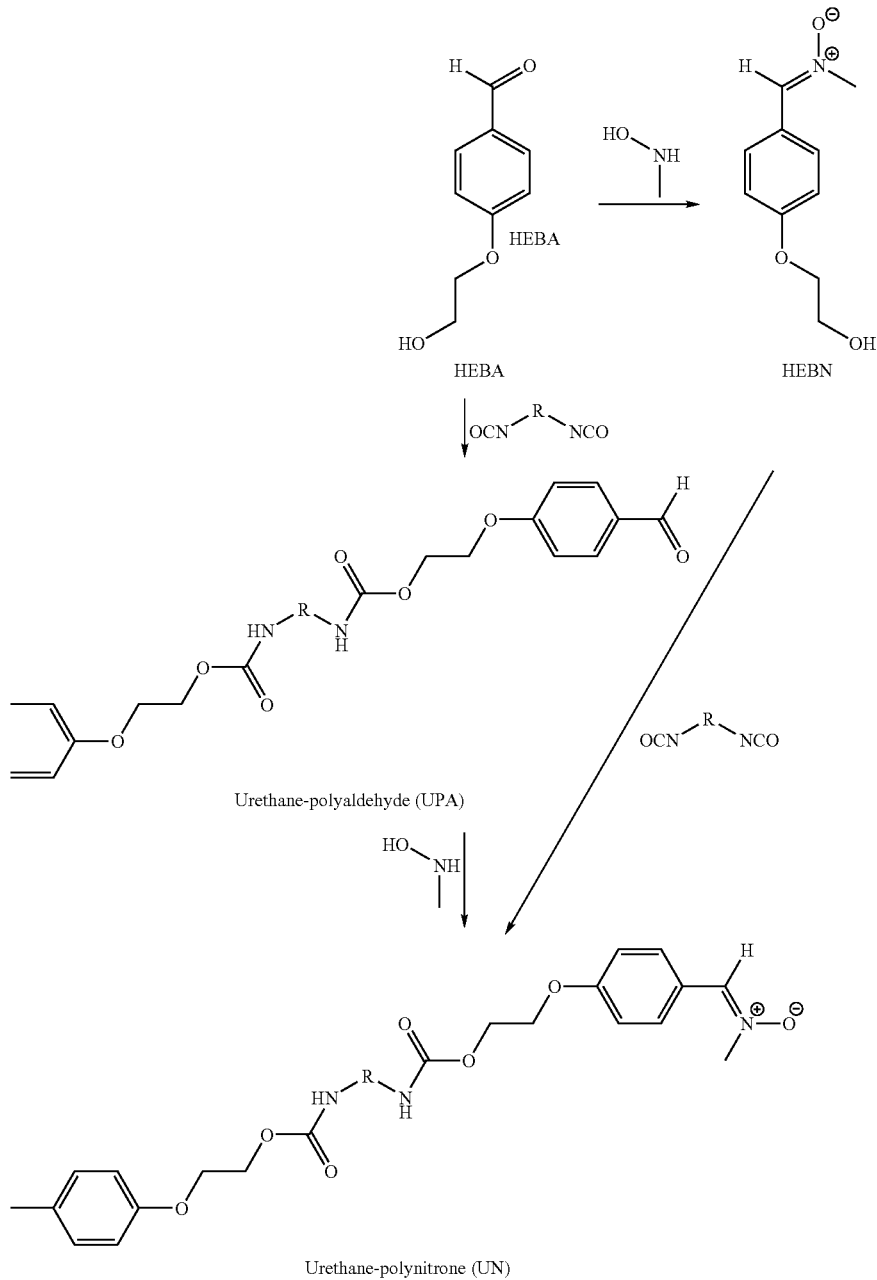

In the reaction scheme above, R is an organic radical; preferably, R is a diphenylmethane radical, a tolylene radical or an isophorone radical, and so the resulting isocyanate is preferably MDI, TDI or IPDI.

The process of the invention for preparing a polynitrone-terminated polyurethane of the invention uses a urethanepolyaldehyde. This means a compound which has two or more urethane groups and two or more aldehyde groups.

The invention hence also provides urethanepolyaldehydes of the general formula V

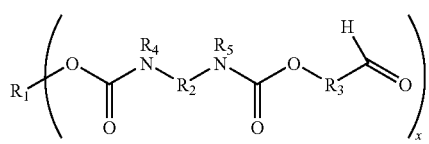

in which x is a natural number from 2 to 12 and $R_1$ to $R_5$ are an organic radical.

Preferably, x is a natural number from 2 to 5, more preferably 3 or 4. $R_1$ and $R_3$ are preferably an optionally substituted linear, cyclic or branched alkylene group, alkyleneoxy group, arylene group, aryleneoxy group, naphthalene group or combinations thereof. $R_4$ and $R_5$ are preferably a hydrogen atom or a $C_1$-$C_6$ alkyl group. $R_2$ is preferably a diphenylmethane radical, a tolylene radical or an isophorone radical.

The invention further provides urethanepolyaldehydes of the general formula VI

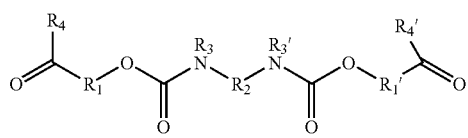

VI in which $R_1$ to $R_4$ and $R_{1'}$ to $R_{4'}$ are an organic radical.

$R_1$ and $R_{1'}$ are preferably an optionally substituted linear, cyclic or branched alkylene group, alkyleneoxy group, arylene group, aryleneoxy group, naphthalene group or combinations thereof. $R_3$, $R_{3'}$, $R_4$, and $R_{4'}$ are preferably a hydrogen atom or a $C_1$-$C_6$ alkyl group, more particularly a hydrogen atom. $R_2$ is preferably a diphenylmethane radical, a tolylene radical or an isophorone radical.

Examples of urethanepolyaldehydes used with preference are the following compounds:

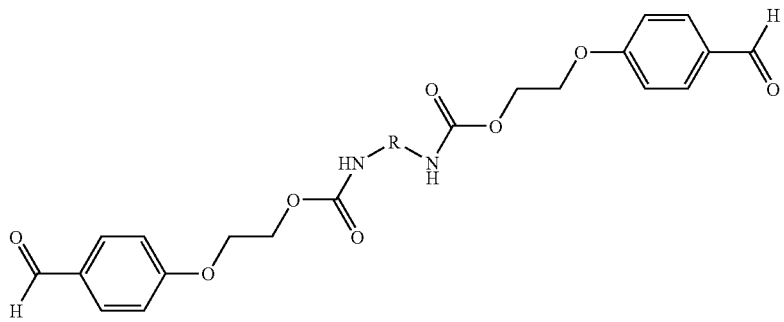

in which R is an organic radical, preferably a diphenylmethane radical, a tolylene radical or an isophorone radical, and

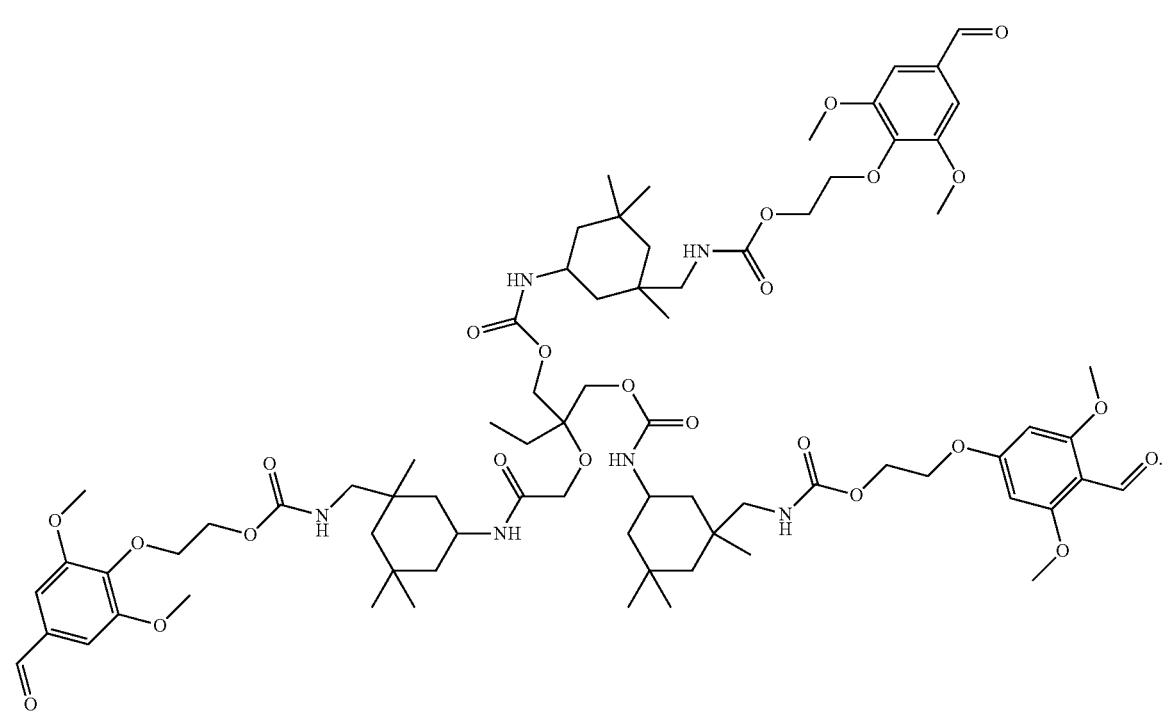

5

Compound 5 is a trifunctional urethanealdehyde. Urethanealdehydes with a functionality of three or more can be obtained by reacting a starter molecule having a functionality of three or more with the hydroxyaldehyde and the polyisocyanate. Examples of suitable starter molecules are, for example, glycerol, trimethylolpropane, and pentaerythritol.

The invention lastly provides processes for preparing an unsaturated polyesterurethane polynitrone, comprising the steps of
(i) reacting an unsaturated polyester with a hydroxyaldehyde compound, and
(ii) reacting with a polyisocyanate, and subsequently
(iii) reacting the unsaturated polyesterurethanealdehyde resulting in step (ii) with an N-alkylhydroxylamine, preferably with N-methylhydroxylamine.

The term "unsaturated polyesterurethane polynitrone" refers to a polyester which has at least one carbon-carbon double bond in the polymer chain and which also has at least two urethane groups and nitrone groups.

With regard to the terms "unsaturated polyester", "hydroxyaldehyde compound", and "polyisocyanate", reference is made to the explanations given above in relation to preferred embodiments.

Likewise provided by the invention are the unsaturated polyesterurethane polynitrones obtainable by the process of the invention.

In summary it may be stated that as a result of the new crosslinking method (i.e., through the inventive use of polynitrones), unsaturated polymers, preferably unsaturated polyester resins, can be cured even at low temperatures. This produces mechanistically stable polymer networks, involving usually neither use of metal catalysts that are injurious to health nor formation of environmentally detrimental elimination products. Crosslinking is rapid and yields products that are stable thermally and mechanistically.

The crosslinking products prepared in accordance with the invention are notable for their extremely diverse usefulness at relatively low preparation cost. They are easy to handle, can be employed alone or, if desired, together with relatively small amounts of other polymers, and can be processed with a large number of fillers, since they have an excellent wetting capacity.

Unsaturated polyesterurethane polynitrones of the invention are advantageous curable one-component systems, comprising not only the unsaturated functions but also the nitrone groups in one polymer framework, and so are thermally self-crosslinkable preferably without an additional crosslinker or catalyst.

The invention is to be explained in more detail by the following examples.

EXAMPLE 1

Synthesis of terephthalaldehyde-bis(nitrone) (DN-0, 1)

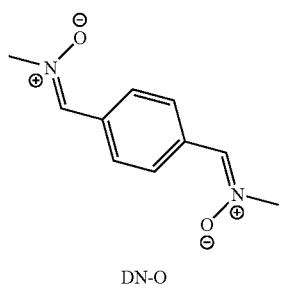

DN-0

(1)

A mixture of 2.95 g (0.022 mol) of terephthalaldehyde and 3.67 g (0.044 mol) of N-methylhydroxylamine hydrochloride in solution in 5 ml of water is added to the NaOH solution (1.76 g, 0.044 mol in 30 ml of ethanol) and the mixture is stirred at room temperature (RT) for 12 hours. The precipitated product is isolated by filtration, washed with water, and then recrystallized from DMF. Melting point: 240° C.

EXAMPLE 2

Synthesis of 1,10-di(4-formylphenoxy)decane (DA-10,2)

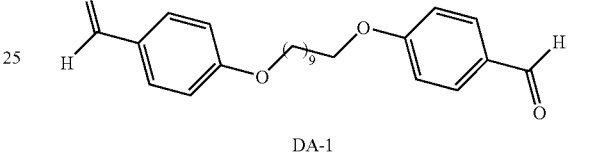

DA-1

(2)

24.4 g (0.2 mol) of p-hydroxybenzaldehyde, 30 g (0.1 mol) of 1,10-dibromodecane and 11.2 g (0.2 mol) of KOH (85%) are heated under reflux in 200 ml of DMF for 30 min. The solution is then allowed to cool to room temperature and is poured into water/ice. The resulting solid is isolated by suction filtration. For purification, the product, which is still moist, is recrystallized from ethanol/water and dried at 70-80° C.

EXAMPLE 3

Synthesis of 4,4'-decanediyldioxydi(N-methyl-p-phenylenenitrone) (DN-10,3)

A mixture of 6.7 g (0.022 mol) of terephthalaldehyde and 3.67 g (0.044 mol) of N-methylhydroxylamine hydrochloride in solution in 5 ml of water is added to the NaOH solution (1.76 g, 0.044 mol in 30 ml of ethanol) and the mixture is stirred at room temperature for 12 hours. The precipitated product is isolated by filtration, washed with water, and then recrystallized from DMF. Melting point: 134° C.

EXAMPLE 4

Synthesis of 4-hydroxyethyloxy-3,5-dimethoxybenzaldehyde (HEBA, 4)

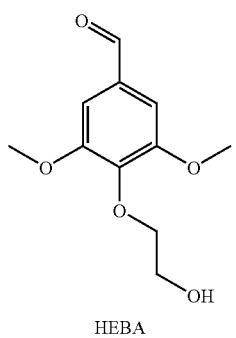

(4)

HEBA

4-Hydroxy-3,5-dimethoxybenzaldehyde (4.99 g, 27.4 mmol), 2-iodoethanol (9.43 g, 54.8 mmol), and potassium carbonate (7.56 g, 27.4 mmol) are added to 50 ml of DMF and left with stirring at 80° C. under a stream of nitrogen for 24 h. After cooling to RT, about 200 ml of water are added to the solution, which is acidified with 10% strength HCl and then extracted with chloroform. After drying with magnesium sulfate, the solvent is removed by distillation and the solid is isolated. For further purification, the solid is purified by column chromatography (flash: ethyl acetate/n-hexane (1:1)).

EXAMPLE 5

Synthesis Example of a Urethanealdehyde (UA-1,5)

A mixture of 1.61 g (0.012 mol) of trimethylolpropane (TMP) and 4.44 g (0.02 mol isophorone diisocyanate) of IPDI and 2.53 g (0.02 mol) of HEBA (4) is introduced in 20 ml of ethyl acetate, and 1-2 drops of dibutyltin laurate (DBTL) are added. Thereafter the reaction mixture is heated to 65° C. under a stream of nitrogen. The reaction mixture is cooled to RT when the samples taken from the reaction solution show no isocyanate band at around 2200 $cm^{-1}$. For the isolation of urethanealdehyde (UA-1, 5), the reaction solution is admixed with about 30 ml of n-hexane, and the urethanealdehyde (4) precipitates. Following the removal of the solvent, the viscous polymer mass obtained is reacted without further purification steps in the next stage (see example 6).

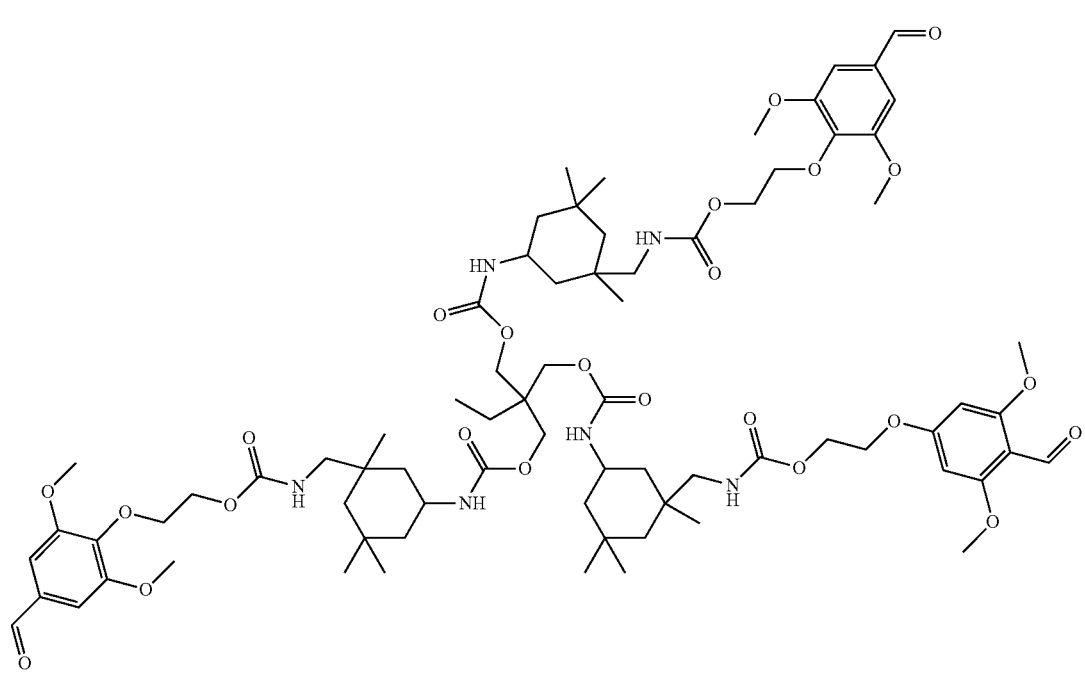

(5)

UA-1

EXAMPLE 6

Synthesis Example of a Urethanenitrone (UA-1, 6)

The urethanealdehyde (5) isolated in example 5 is suspended in 25 ml of 2N NaOH solution (in ethanol). The suspension is then admixed with 2.24 g (25.9 mmol) of N-methylhydroxylamine hydrochloride in solution in 5 ml of water and left to stir at RT for 12 h. The precipitated product is isolated by filtration, washed with water, and dried in a drying cabinet under vacuum at 40° C.

IR (diamond) 3311 (—NH—), 2948 (C—H), 1695 (O—CO—NH), 1576 (C=N), 1152 (N—O) Maldi-TOF: 1564, 1700, 1860, 2020, 2141 (m/z)

EXAMPLE 7

Characterization of a Commercially Available Unsaturated Polyester UP-1 (7)

UP-1 (7) is the commercial product from the company DSM (Uracross P 3125), with terephthalate/fumarate/neopentylglycol components.

| | |
|---|---|
| Acid number: | <5 mg KOH/g |
| Viscosity: | 30-50 Pas |
| Glass transition temperature: | 45° C. |

EXAMPLE 8

Synthesis of an Unsaturated Polyester UP-2 (8)

A mixture of 1.96 g (0.02 mol) of maleic anhydride (MA), 2.36 g (0.02 mol) of hexanediol (Hex), 0.1% by weight of toluenesulfonic acid hydrate, and 1% by weight of BHT stabilizer is heated under reflux for 30 min in a microwave (CEM) at 200° C. with a microwave power of 300 watts. To purify it of low molecular mass starting components, the reaction product is dissolved in acetone and then precipitated by addition of petroleum ether (60/80). After the solvent has been decanted off, the unsaturated polyester is dried under vacuum.

(6)

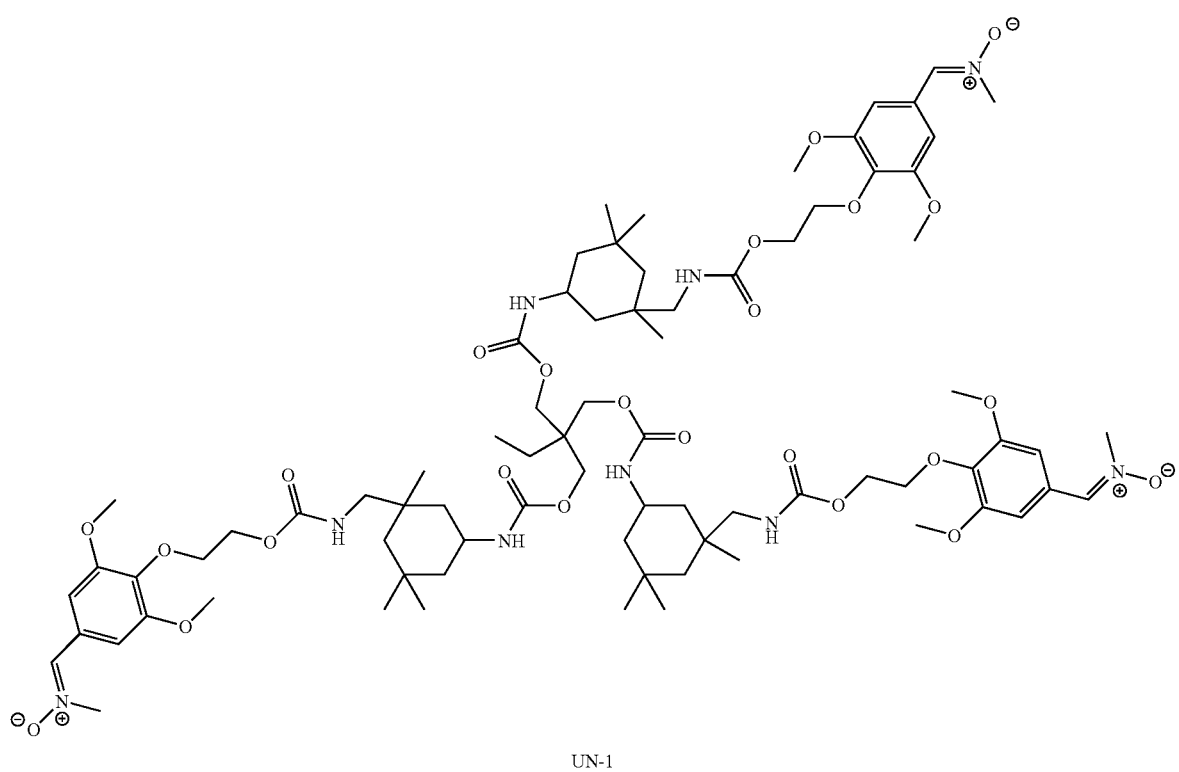

UN-1

| | |
|---|---|
| Acid number: | 74.06 mg KOH/g |
| GPC: | Mn: 750; $M_w$: 1500; PD: 2 |
| Glass transition temperature $T_g$: | −47° C. (DSC) |

EXAMPLE 9

Preparation of a Hydroxy-Terminated Unsaturated Polyester (UP-3, 9)

A mixture of 32.8 g (0.42 mol) of diethylene glycol, 38.2 g (0.23 mol) of terephthalic acid, and 0.05 g (26.3 mmol) of p-toluenesulfonic acid monohydrate were heated at 190-200° C. with vigorous stirring in a flask with a water separator attachment. When the terephthalic acid was fully dissolved, the mixture was cooled to 160° C. and 0.05 g of BHT stabilizer and 11.8 g (0.1 mol) of maleic anhydride were added. The mixture was heated again slowly to 180-190° C. and maintained with stirring until the acid number determined is about 20 mg KOH/g. After a further hour of heating at 180-190° C. under vacuum and with subsequent cooling to RT, a transparent unsaturated polyester was obtained with the following properties:
Acid number: 16.2 mg KOH/g
$T_g$: 38° C. (DSC)

EXAMPLE 10

Preparation of an Unsaturated Polyesterurethanealdehyde (UP-UA-2, 10)

51 g (0.017 mol) of the unsaturated polyester prepared in example 9 (UP-3, 9) and 10.86 g (0.05 mol) of 4-(2-hydroxyethyloxy)benzaldehyde were heated to 120° C. With stirring, 2-3 drops of dibutyltin laurate were added and then 18 g of IPDI (isophorone diisocyanate) were added slowly dropwise at 120° C. The mixture was stirred further at 120° C. until the samples taken showed an NCO content of less than 0.1% by weight.

EXAMPLE 11

Preparation of an Unsaturated Polyesterurethane Nitrone (UP-UN-1, 11)

10 g of the UP-UA-1 (10) finely ground in example 10 were dispersed in 30 ml of ethanol, and this dispersion was admixed slowly dropwise with a solution in 10 ml of water of 0.30 g (7.5 mmol) of NaOH and 0.62 g (7.5 mmol) of N-methylhydroxylamine hydrochloride, and left with stirring overnight at RT. The precipitated solid was filtered, washed with water, and dried under vacuum.

The resulting unsaturated polyesterurethane nitrone is a 1K system, which is crosslinked in example 15.

EXAMPLE 12

The Crosslinking of the Unsaturated Polyester UP-1 (7) with the Polynitrone DN-0 (1)

9 g of UP-1 (7) (DSM, Uracross P 3125) and 1 g of DN-0 (1) are ground to a fine powder in a hand mill and then placed between two metal plates in a rectangular Teflon mold. After 1 h of oven storage at 120° C., a very hard, white and opaque molding compound was obtained. The molding compound obtained is solvent-resistant with respect to chloroform, THF, and acetone.

EXAMPLE 13

The Crosslinking of UP-2 (8) with DN-0 (1)

0.92 g of UP-2 (8) and 0.08 g of DN-0 (1) were mixed to form a dispersion and then stored in a prefabricated Teflon mold at 80° C. for 5 h. An elastic film was removed from the Teflon mold. The film was solvent-resistant.

EXAMPLE 14

The Crosslinking of UP-2 (8) with DN-10 (3)

0.9 g of UP-2 (8) and 0.1 g of DN-10 (3) were mixed to form a dispersion and then stored in a prefabricated Teflon mold at 80° C. for 6 h. An elastic film was removed from the Teflon mold. The film was solvent-resistant.

EXAMPLE 15

The Self-Crosslinking of UP-UN-1 (11)

5 g of the unsaturated polyesterurethane nitrone UP-UN-1 (11) prepared in example 11 were ground to a fine powder in a hand mill and then placed between two metal plates in a rectangular Teflon mold. After 2 h of storage at 120° C., a transparent, solvent-resistant molding compound was obtained.

Figure 2:
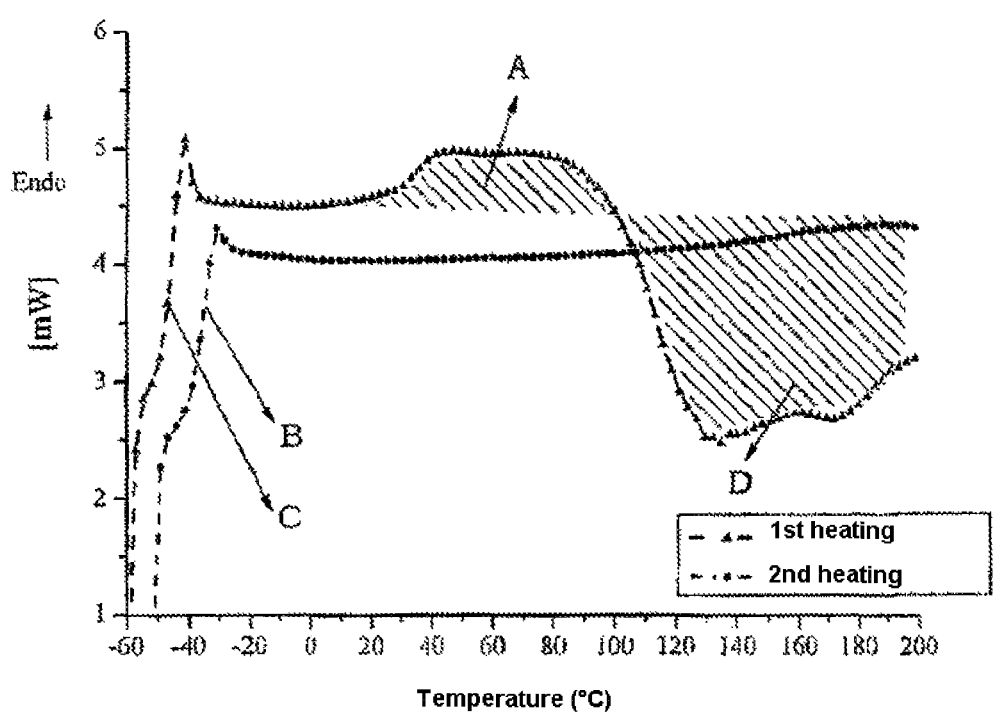
FIG. 2 depicts the results of self-crosslinking, specifically DSC heating curves.

Discussion of the Results:

The crosslinking of the mixture of UP-2 (8, 90% by weight) and DN-10 (2, 10% by weight) (example 13) was monitored by means of DSC measurement at a heating rate of 10° C./min between −60 and 200° C. The DSC curves obtained are shown in FIG. 2.

A: dissolution process
B: $T_g$=−34° C. (crosslinked)
C: $T_g$=−47° C. (not crosslinked)
D: exothermic crosslinking The first DSC heating curve in FIG. 2 shows that UP-2 (8) prior to crosslinking has a $T_g$ value of −47° C. Immediately after the homogenization process, at about 80° C., crosslinking of the mixture occurs, and is readily perceptible in the first heating curve through the exothermic peak. The second heating curve shows no exothermic peak, owing to the crosslinking process having proceeded to completion, and, as a consequence of the restricted chain mobility due to crosslinking, shows a $T_g$ value (−34° C.) which is shifted by about 13° C. in comparison to the first heating curve.

Figure 3:
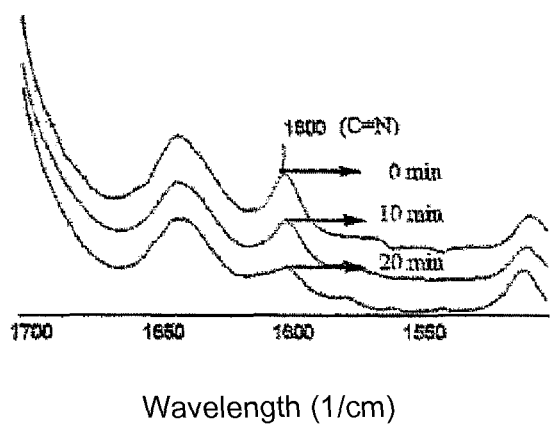
FIG. 3 depicts IR spectra conducted to support the DSC investigation.

To support the above DSC investigation, the kinetics of the cycloaddition of DN-10 (2) to UP-2 (8) were also monitored by means of IR spectroscopy. The IR spectra in FIG. 3 show a continuous decrease in the absorption band at 1600 cm$^{-1}$, which can be assigned to the C=N group of DN-10 (2).

Figure 4:
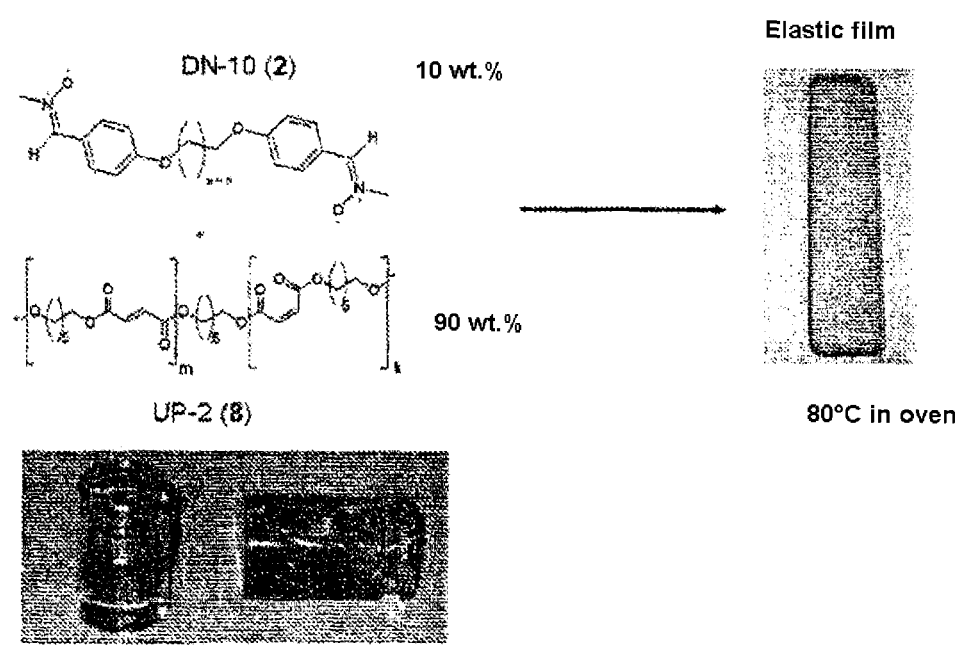
FIG. 4 depicts the IR spectra of the crosslinking of the unsaturated polyester UP-2 (8) with DN-10 (2) of Example 13.

The IR spectra clearly show the rapid progress of the crosslinking reaction. In FIG. 4 the crosslinking of the unsaturated polyester UP-2 (8) with DN-10 (2) (example 13) has been depicted.

The results can be summarized as follows:

The crosslinking method according to the invention provides new possibilities for the development of new materials in accordance with an environmentally friendly variant. The combination of, for example, unsaturated polyester and polyfunctional nitrones (=polynitrones) can be exploited in the following sectors for the development of new products:
- development of new adhesives (e.g., hotmelt adhesives);
- in the furniture sector. As a result of rapid curing and virtually 100% solids, the application of very thick films in one operation is possible;
- preparation of fast-curing and readily sandable knifing fillers (automotive refinishing, wood-processing and metal-processing industry);
- preparation of sprayable high-build fillers (automotive refinishing, wood-processing and metal-processing industry);
- production of glass fiber-reinforced polyester components (GRP polyester), e.g., in ship building;
- development of thermally curable coatings, especially waterborne coatings;
- development of self-curing powder coatings, such as nitrone-terminated urethane-unsaturated polyester, for example.

As well as the stated sectors, the invention provides an optimum solution for the matting of curable powder coatings. This relates to the inventive use of polynitrones as matting agents. It has unexpectedly been found that the curable powder coatings, especially UV-curable powder coatings, exhibit very good matting properties as a result of the addition of polynitrones.

The addition, at low levels, of various polynitrones to the UP powder coating (P-UP, 9) led after UV curing to surfaces where, in addition to the good surface profile, the gloss of the surface was greatly reduced.

The use of polynitrones as matting agents is investigated further exemplarily in the following examples.

COMPARATIVE EXAMPLE 16

Preparation of the UP Powder Coating (P-UP, 12)

TABLE 1

Formulation of the UP powder coating (P-UP, 12)

| Constituents | UP powder coating P-UP (12) (% by wt.) |
| --- | --- |
| Uracross P 3125 ® (DSM) Unsaturated polyester (UP-1, 8) | 83 |
| Uracross P 3307 ® (DSM) Vinyl ether urethane (VEU, 10) | 17 |
| Powdermate EX 486 ® (Flow control agent) | 2 |
| Irgacure 2959 ® (Photoinitiator) | 1 |

The mixture of the composition listed in the table is processed in accordance with the procedure described in FIG. 1 to give the powder coating P-UP (12).

COMPARATIVE EXAMPLE 17

P-UP (12) Powder Coating without Addition of Polynitrones

The powder coating P-UP (12) is applied to various surfaces (glass, PET films, phosphated steel). After heating in an oven at 140° C. for 15 minutes and subsequent UV curing, all of the applied surfaces exhibit very high gloss (60° gloss: >90%).

EXAMPLE 18

P-UP (12) Powder Coating with Addition of Polynitrone DN-10 (2)

The completed powder coating P-UP (12) was admixed with the polynitrone DN-10 (2), in dry form, the finely ground polynitrone having an average particle size of about 40-50 μm. Following physical homogenization, the material was applied to various surfaces (glass, PET films, phosphated steel plate). The panels thus applied are heated in an oven at 140° C. for 15 min and then cured by means of UV radiation. In this case the weight fraction of polynitrone is 1-5% of the total amount of powder coating. All of the applied surfaces exhibit a sharp reduction in gloss (60° gloss: <50%).

Discussion of the Matting Process

Figure 5:
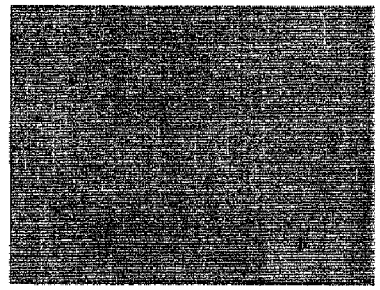
FIG. 5 depicts a light-micrograph of powder-coated glass surfaces with (right side) and without (left side) addition of polynitrone DN-10 (2).
Figure 5:
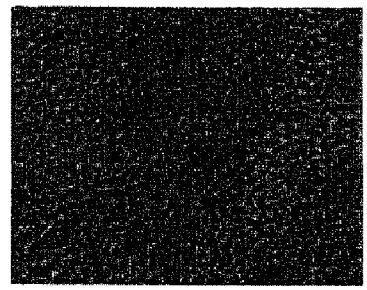

The addition, at low levels, of polynitrones (DN-10, 2) to the UP powder coating (P-UP, 12) led after UV curing to surfaces where, in addition to the good surface profile, the gloss of the surface was greatly reduced. FIG. 5 shows powder-coated glass surfaces with and without addition of polynitrone DN-10 (2). FIG. 5 is a light-micrograph of the coated glass surface once without (left) and once with (right) addition of polynitrone DN-10 (2).

Figure 6:
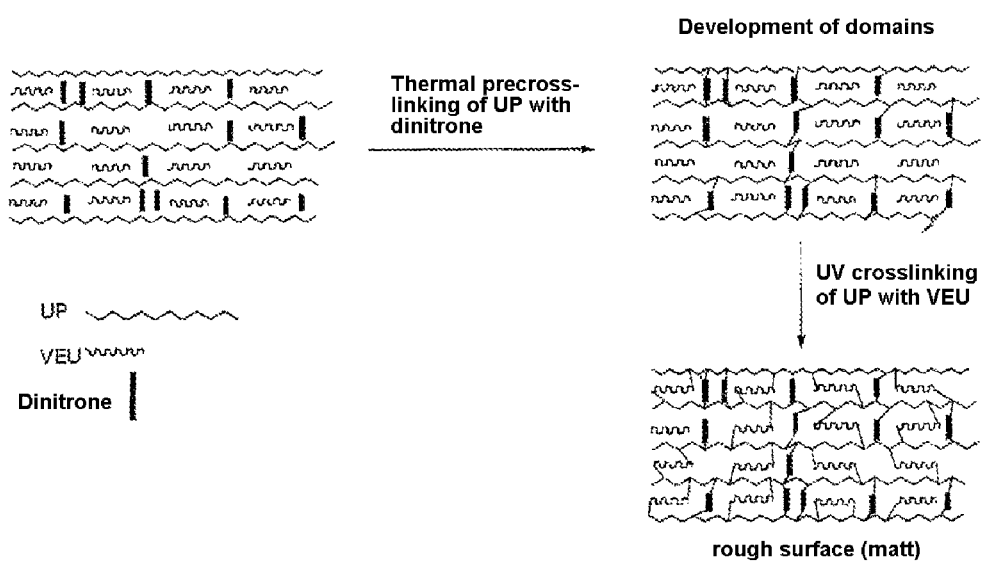
FIG. 6 depicts the mechanism of matting with respect to UP powder coat (P-UP, 12) and the composition thereof being indicated in the table of comparative Example 16.

Here, the principle known as "dual cure" is employed, where the powder coating is first preliminarily fixed or structured by the cycloaddition of the polynitrone to the double bonds of the binder at low temperatures (50-140° C.) and subsequently is crosslinked by UV radiation. The locally produced microstructures result in a rough surface profile, as a result of which, owing to the diffuse light reflection at the surface, the gloss of the surface is greatly reduced. In FIG. 6, the mechanism of matting in respect of the UP powder coating investigated (P-UP, 12) has been shown diagrammatically, the composition thereof being indicated in the table of comparative example 16.

Accordingly the invention also provides for the use of polynitrones as matting agents. As well as the urethane polynitrone powder coatings described, powder coating systems based on the systems below can also be matted by the addition of polynitrones.

Acrylate/methacrylate-functionalized polyesters

Acrylate/methacrylate-functionalized unsaturated polyesters

Unsaturated polyester urethane (meth)acrylates, which are described, for example, in U.S. Pat. No. 6,284,321B1.

All of the classes of powder coating described are preferably prepared in accordance with the procedure set out in FIG. 1 and then are mixed with the corresponding amounts of polynitrones and physically homogenized, before being applied to the various surfaces.

In summary it may be stated that the invention relates to a new (environmentally compatible) crosslinking method in which, through the use of polynitrones, the industrially important resins, such as unsaturated polyesters and (meth)acrylates, for example, can be cured and/or structured at low temperatures. The invention resolves in particular the problems of the coating manufacturers in switching from conventional to environmentally friendly coating methods.

The invention claimed is:

1. A method for using polynitrones for crosslinking unsaturated polymers, comprising:
   (i) providing a curable composition, comprising a polynitrone, an unsaturated polymer, and optionally one or more selected from fillers and pigments;
   (ii) curing the composition at temperatures of 20 to 180° C.; and
   (iii) producing a crosslinking product;
      wherein the curable composition is a 2-component system in the form of two compounds and is comprised of the polynitrone and the unsaturated polymer, and wherein the polynitrone is a compound according to formula I,

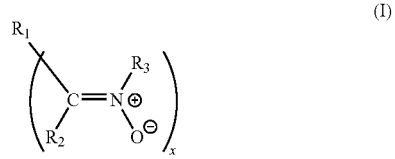

wherein x is 2;
R$_1$ is

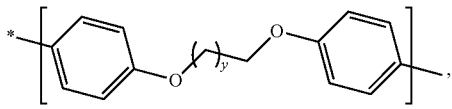

wherein y is from 1 to 12; and R$_2$ and R$_3$ are independently selected from the group consisting of hydrogen and C$_1$-C$_6$ alkyl group.

2. The method of claim 1, wherein the curing temperature is 50 to 150° C.

3. The method of claim 1, wherein the method further comprises changing the mechanical and/or optical properties of the unsaturated polymer.

4. The method of claim 3, wherein the changing further comprises hardening and/or matting the unsaturated polymer.

5. The method of claim 1, wherein the unsaturated polymer has at least one unsaturated carbon-carbon bond in the polymer chain and is selected from the group consisting of polyolefins, polystyrene, polyvinyl alcohol, polyvinyl acetate, polyalkylene glycol, polyethylene oxide, polypropylene oxide, polyacetals, polyurethanes, polyureas, polyamides, polycarbonates, polyketones, polysulfones, phenol-formaldehyde resins, polyesters, polyester acrylates, polyurethane acrylates, cellulose, gelatin, starch and mixtures thereof.

6. The method of claim 1, wherein the polynitrone is present in an amount of 1% to 20% by weight, based on the total weight of the composition.

7. The method of claim 1, wherein the crosslinking product is selected from an adhesive, a knifing filler, a sprayable high-build filler, a powder coating and coating based on solvent systems.

8. The method of claim 1, wherein the crosslinking product is used for producing dental materials, household appliances, kitchen worktops, bath tubs, wash basins, and glass fiber reinforced polyester components.

9. The method of claim 8, wherein the glass fiber reinforced polyester components are used in shipbuilding.

* * * * *